United States Patent
Pauluth et al.

[11] Patent Number: 6,137,576
[45] Date of Patent: Oct. 24, 2000

[54] OPTICAL TRANSDUCERS BASED ON LIQUID CRYSTALLINE PHASES

[75] Inventors: Detlef Pauluth, Ober-Ramstadt; Joachim Krause, Dieburg; Günter Gauglitz, Tübingen; Bernd Drapp, Reutlingen, all of Germany

[73] Assignee: Merck Patent Gesellschaft mit Beschrankter Haftung, Germany

[21] Appl. No.: 09/122,884

[22] Filed: Jul. 28, 1998

[51] Int. Cl.$^7$ .................................................. G01B 9/02
[52] U.S. Cl. .......................................... 356/361; 356/345
[58] Field of Search .................................. 356/345, 359, 356/360, 361

[56] References Cited

U.S. PATENT DOCUMENTS

| | | |
|---|---|---|
| 4,041,847 | 8/1977 | Spengler . |
| 5,324,449 | 6/1994 | Kurmeier et al. . |

OTHER PUBLICATIONS

*Fresenius J. Anal. Chem.* (1994) 350:577–581, F.L:. Dickert et al.
*Fresenius J. Anal. Chem.* (1997) 357:27–31, F.L. Dickert et al.
"Integrated optical devices with liquid crystal overlays for the sensing of volatile organic compounds", pp. 1–7; B. Drapp et al.

"Characterisation of nematic liquid crystals as sensitive materials on integrated optical devices for the sensing of hydrocarbons", B. Drapp et al.

*Primary Examiner*—Robert H. Kim
*Attorney, Agent, or Firm*—Millen, White, Zalano & Branigan, P.C.

[57] ABSTRACT

Optical transducers for measuring a contaminant in a gas are disclosed, whereby said contaminant interacts with a liquid crystalline phase as a sensing element in a flow cell. According to the invention nematic crystalline phases on a orientation layer are used. Means are provided to measure or to detect changes of the refractive index of said liquid crystalline phase caused by interaction of said contaminant with said liquid crystalline phase. In preferred embodiments the means for measuring or for detecting the refractive index is a Mach-Zehnder interferometer, a grating coupler, or a device for e.g. visual detection, whereby the flow cell is placed between two linearly polarizing filters, and whereby the two axis of polarization are crossed. Furthermore optical transducers are disclosed, which contain an isotropic dopant in a liquid crystalline phase. Also disclosed is the use of these optical transducers for detecting or measuring contaminants in gases using an optical transducer according to the invention.

26 Claims, 6 Drawing Sheets

"Length of Interaction"

OPTICAL TRANSDUCERS BASED ON LIQUID CRYSTALLINE PHASES

FIELD OF INVENTION

This invention is related to transducers containing a liquid crystalline phase as sensing element. Due to interactions with the analyte the refractive index of the liquid crystalline phase, especially its birefringence, is influenced. Such transducers are useful for optical sensing of organic solvents in gases.

BACKGROUND OF THE INVENTION

The need for sensors for measuring contamination of air or other gases caused by solvents, e.g., aromatic solvents like benzene, toluene, xylenes, or e.g., aliphatic solvents or coolants/refrigerants like propane or hexane, or e.g., halocarbons, like tetrachloroethylene, dichlorodifluoromethane, 1,1,1,2-tetrafluoroethane, or 1,1,1,2,3,3,3-heptafluoropropane is increasing. Among other methods, liquid crystal (LC) layers have been used in sensing devices for such purposes. When the contaminated air or other gas (gas phase) gets into contact with a LC-phase (host phase) these contaminants can enter the host phase forming a guest phase within the host phase. The distribution of said contaminant between the gas phase and the host phase is influenced inter alia by the vapor pressure of the contaminant and by the interaction between guest and host phases. The contaminant in the host phase changes mass and viscosity of the host phase, as well as its density. These changes can be measured using a quartz micro balance (QMB) or by using acoustic wave sensors (AWS). Devices for measuring contaminants in gas phases using such principles are disclosed in *Fresenius J. Analyt. Chem.* 357, 27–31 (1997) and in earlier publications. So far optical effects arising from the interactions of host and guest phases used for measuring contaminants in gases are only based on measuring the absorptivity and its changes due to the interaction between host and guest phases using cholesteric LC phases. Devices containing such cholesteric LC's used for this kind of measurements are based on multiwavelength spectroscopy and are disclosed in *Fresenius J. Analyt. Chem.* 350, 577–581(1994). The authors of this study stress in much detail the necessity of improved algorithms necessary for data reduction in multiple wavelength absorbance measurements. It is noteworthy that later (1997) the same authors moved to non-optical principles for measuring host-guest phase interactions (see *Fresenius J. Analyt. Chem.* 357, 27–31 (1997) mentioned above).

SUMMARY OF THE INVENTION

Devices according to the present invention contain a sensing element, e.g. the liquid crystal layer. By interaction with the sensing element, the analyte, e.g., toluene, modifies a physical or chemical parameter of the sensing element. By means of a transducer these changes are transformed into signals, which can easily be measured, e.g., a light intensity, a voltage, or an electrical current.

An object of the present invention is to provide simpler detection devices for detecting contamination of gases, particularly by solvents. It has been shown that detecting devices based on measuring changes of refractive index, especially of birefringence, can be much simpler compared to the devices for multi wavelength measurements necessary in prior art.

Upon further study of the specification and appended claims, further objects and advantages of this invention will become apparent to those skilled in the art.

In nematic liquid crystals the birefringence is related to the order parameter of the system. It was found that the penetration of a liquid crystal film by an analyte disturbs the original alignment and decreases the order parameter. An analyte (the contaminant) entering the LC-phase changes the refractive indices of a liquid crystal by decreasing the order parameter crystal. The underlying principle was presented by the inventors at the OLC'97 (International Topical Meeting on Optical Properties of Liquid Crystals; Heppenheim, Germany, on Sep. 23, 1997).

It was later discovered that the sensitivity of a liquid crystal film can be increased by doping said film with an isotropic material.

The novel application of using the change in refractive index can be used in different types of optical transducers, which are basically known in the art. Among these are transducers using the emanescent field effect, e.g. interferometers especially of the Mach-Zehnder type. Other devices useful to measure effects based on changes of refractive index are grating couplers. In displays based on LC's the birefringence of LC-layers can be used to create dark and light areas in reflected or transmitted light. Such devices can be used to monitor a threshold value for contaminants. Details of such applications are given below.

The invention includes optical transducers for measuring a contaminant in a gas, whereby said contaminant interacts with a liquid crystalline phase as sensing element in a flow cell, whereby said liquid crystalline phase is a nematic crystalline phase on an orientation layer and means are provided to measure or to detect changes of the refractive index of said liquid crystalline phase caused by interaction of said contaminant with said liquid crystalline phase. In preferred embodiments the means for measuring or detecting changes of the refractive index is a Mach-Zehnder interferometer, a grating coupler, or a device for, e.g., visual or photometric detection, whereby the flow cell is placed between two linearly polarizing means, and whereby the two axes of polarization are crossed. The invention is also directed to optical transducers as described above, wherein an isotropic dopant is introduced into the liquid crystalline phase.

The invention is further directed to methods to detect and/or measure contaminants in gases using an optical transducer as described above.

Figure 4:
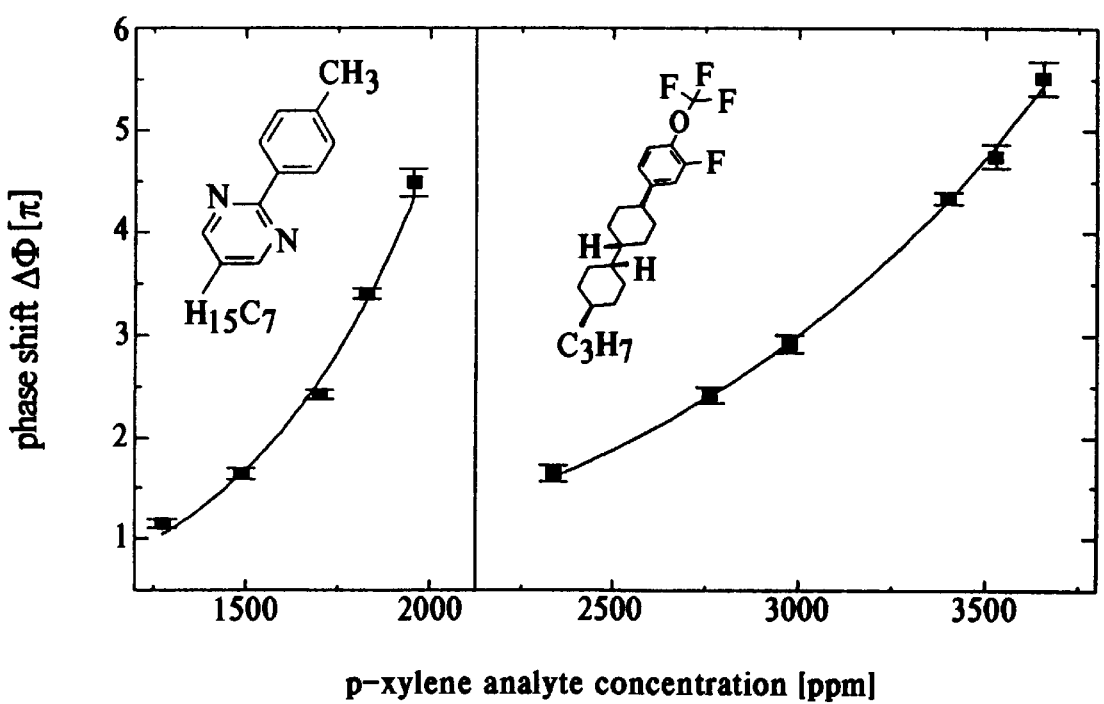

Calibration graphs (phase shift vs. concentration) for p-xylene using two different LC systems are given in FIG. 4.

Figure 5:
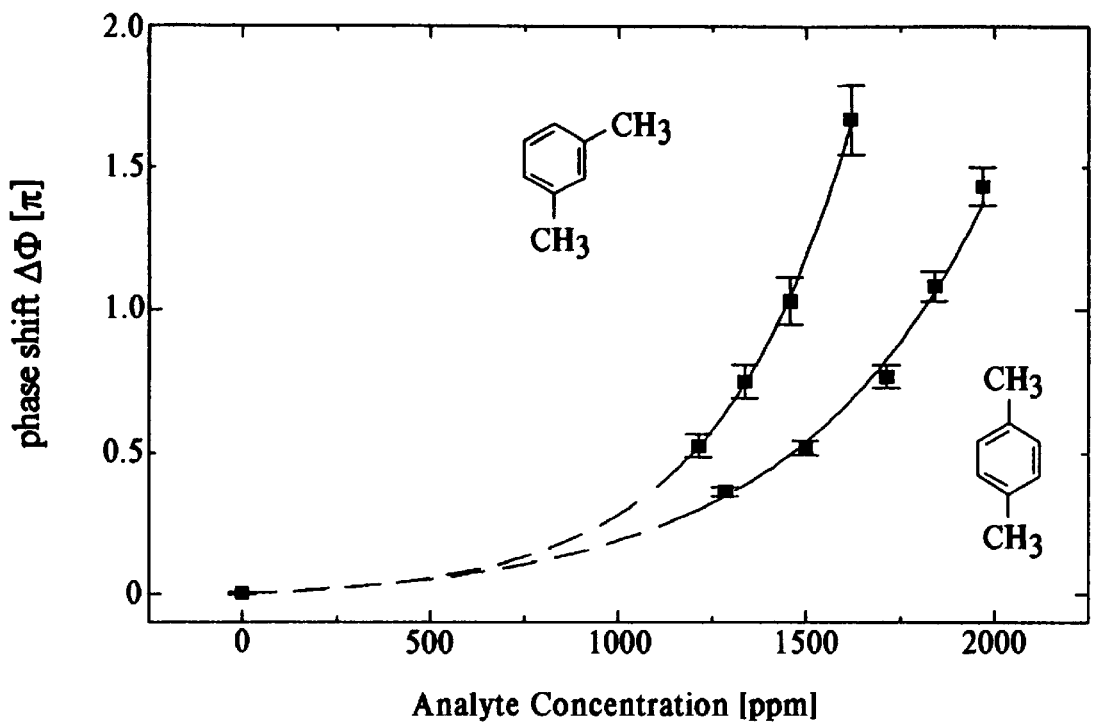

FIG. 5 shows calibration graphs (phase shift vs. concentration) for m-xylene and for p-xylene.

Figure 6:
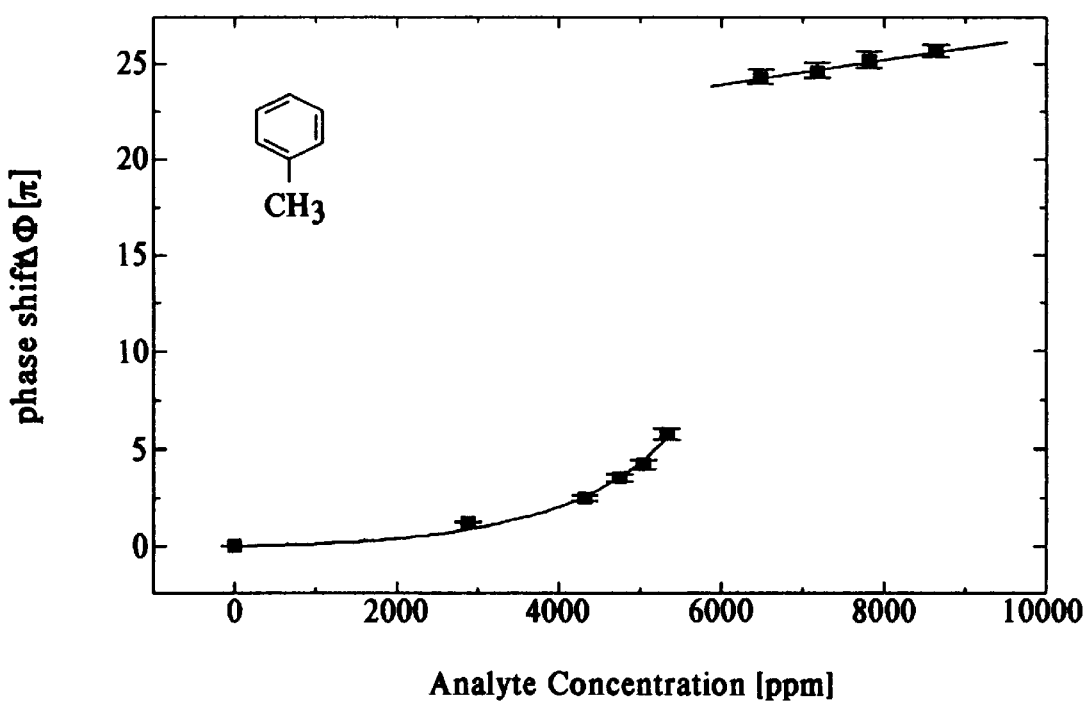

A calibration graph (phase shift vs. concentration) for toluene is given in FIG. 6; the system shows a phase transition at about 6000 ppm toluene.

Figure 7:
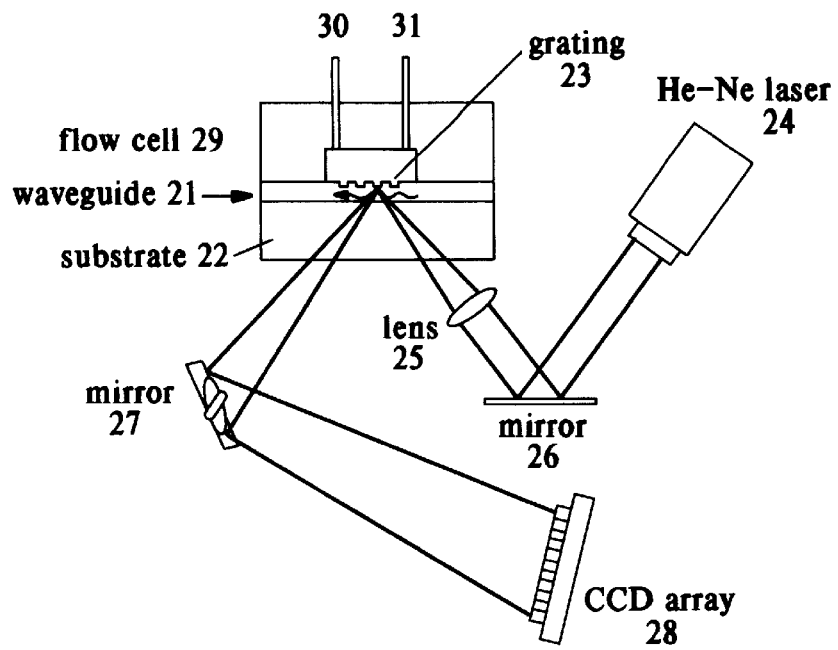

FIG. 7 depicts the experimental set-up for measuring the interaction between analytes and LC phase using a grating coupler.

Figure 8:
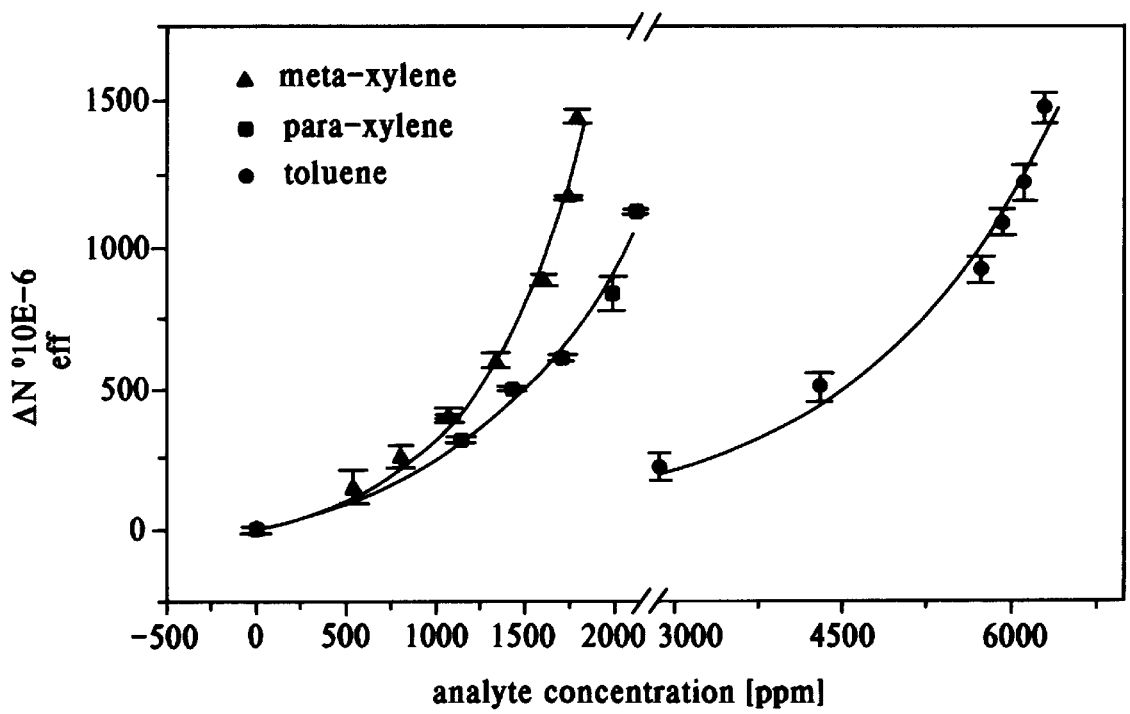

FIG. 8 shows a calibration graph using a grating coupler as measuring device.

Figure 9:
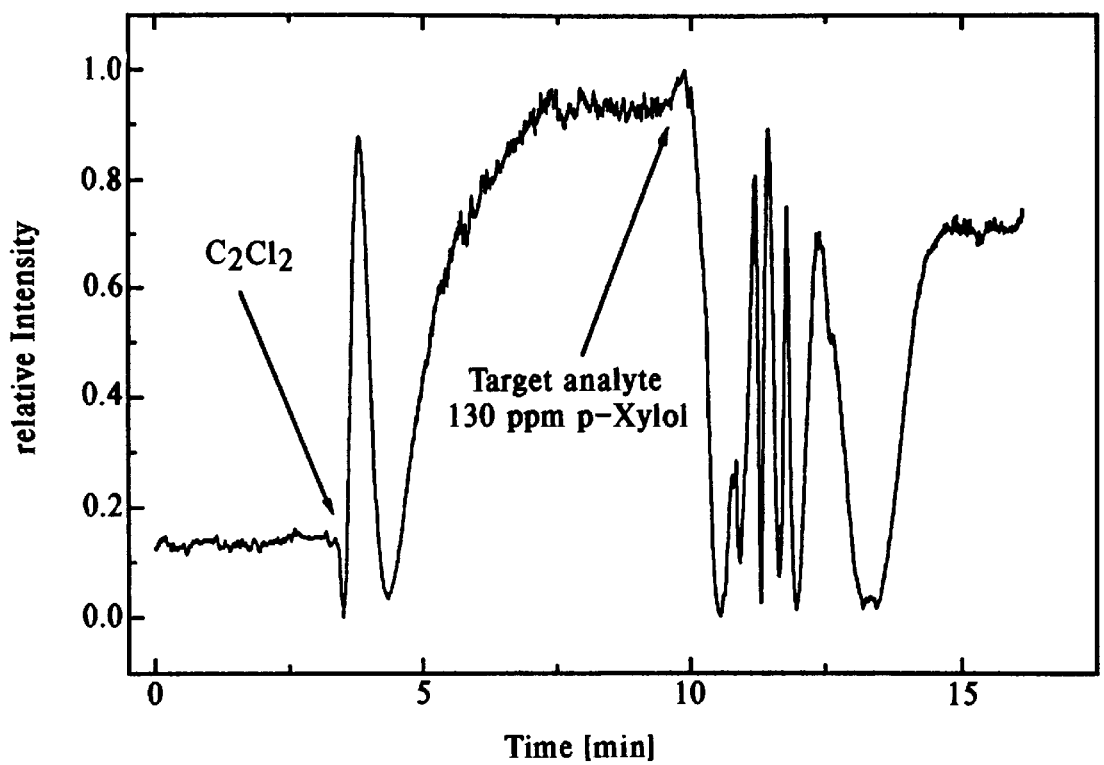

FIG. 9 depicts the response curve of a detection system doped with tetrachloroethylene, thus 130 ppm p-xylene can be detected.

Figure 10:
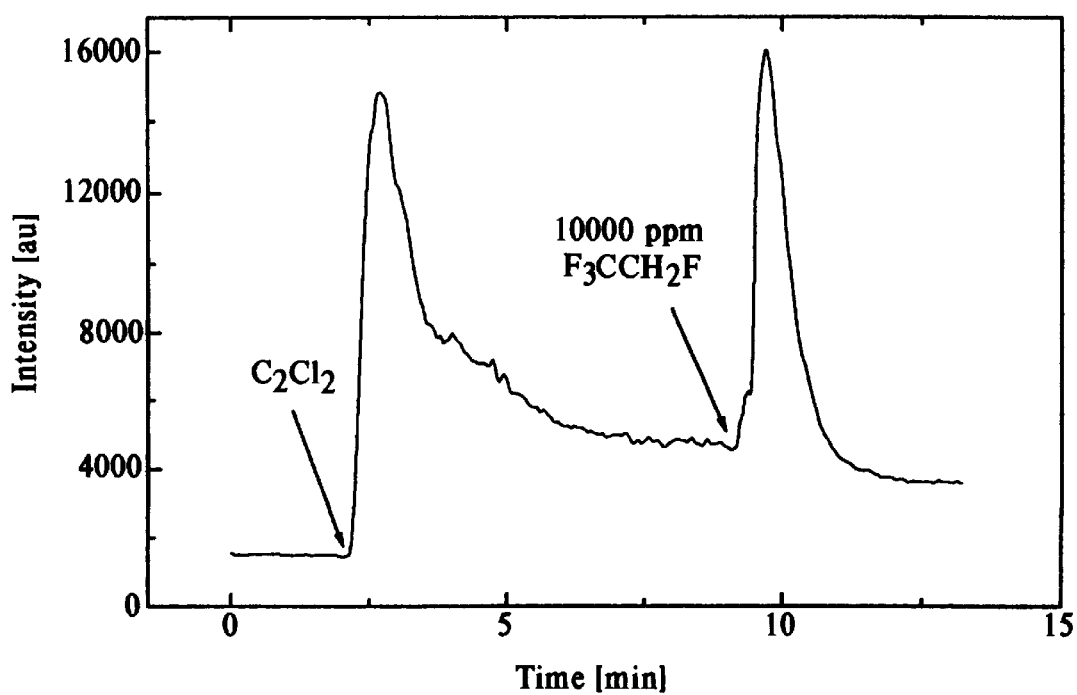

FIG. 10 depicts the response curve of a detection system doped with tetrachloroethylene whereby 10,000 ppm $F_3CCH_2F$ can be detected.

Figure 11:
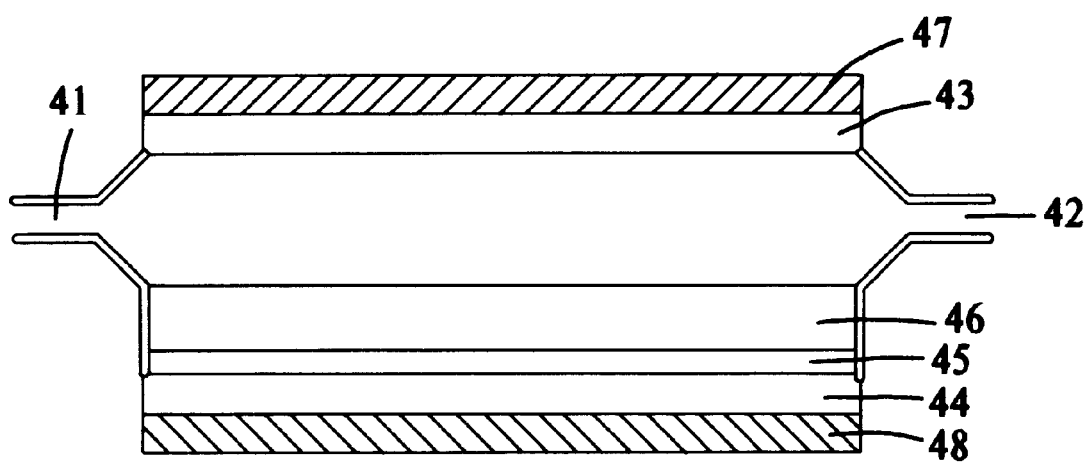

FIG. 11 shows a grossly simplified detection system useful to monitor threshold values for contaminants.

DETAILED DESCRIPTION OF THE INVENTION

It has been found that an analyte penetrating into a liquid crystal layer changes both the density as well as the molecular orientation of the layer. Thus the analyte can be detected by measuring the change in refractive indices. Planar optical waveguides and the evanescent field of the guided light can be utilized to probe the refractive index of the liquid crystal. The liquid crystals were used in an homogeneous planar orientation on the waveguide surface. The original orientation was induced by modifying the waveguide surface with an orientation layer as known in the art, e.g., with a unidirectional rubbed polyimide layer.

Among the measuring devices useful as sensitive bulk refractometers two measuring principle have proven useful:

a) The integrated Mach-Zehnder interferometer is based on two parallel strip waveguides, the measuring and the reference waveguide. y-branch couplers are used to split and to combine the two waveguides. Except for the measuring window, which is covered by the liquid crystal layer, the device is covered with a patterned SiO2 layer. The light intensity, I (candela), outcoupled from the device can be described by equation 1

$$I = \frac{I_0}{2}\left(1 + \cos\left(\frac{2\pi}{\lambda}L(N_{meas} - N_{ref})\right)\right) \quad \text{eq. 1}$$

where $N_{meas}$ and $N_{ref}$ denote the effective refractive index of the measuring arm and the reference arm, respectively of the waveguide. L (meters) stands for the length of the silica free measuring window, λ(nm) is the operating wavelength of the interferometer, and $I_o$ is the light intensity incoupled to the device.

b) The integrated optical grating coupler is based on a grating structured film waveguide. The light focused upon the grating is coupled into the waveguide when equation 2 is complied:

$$N_{eff} = n_{med}\sin\alpha + \frac{m\lambda}{\Lambda} \quad \text{eq. 2}$$

whereby $N_{eff}$ stands for the refractive index of the waveguide, Λ is the operating wavelength of the incoupled light, m is an integer indicating the coupling mode, Λ denotes the grating constant, α is the coupling angle of the incident light and $n_{med}$ means the refractive index of the liquid crystal with respect to the polarization state of the incoupled light. The grating coupler is used in reflection mode, essentially as described by A. Brandenburg and A. Gombert (1993) in *Sensors and Actuators B* 17, pages 35–40, and by J. Piehler, A. Brandenburg, A. Brecht, E. Wagner, and G. Gauglitz (1997) *Applied Optics* 36, pages 6554–6562.

Evanescent field based transducers useful in conducting the invention, other than the Mach-Zehnder interferometer and the grating coupler described above, are known in the art; among these are:

integrated optics (IO) Young interferometer as described by A. Brandenburg and R. Henninger (1994) in *Appl. Optics* 33, pages 5941–5947;

IO difference interferometer as described by Ch. Stamm and W. Lukosz (1993) in *Sensors and Actuators B* 11, pages 177–181;

bidifractive grating coupler as described by Ch. Fattinger et al. (1995) in *Opt.Eng.* 34, pages 2744–2753;

planar waveguide IO surface plasmon resonance as described by R. D. Harris and J. S. Wilkinson (1995) in *Sensors and ActuatorsB* 29, pages 261–267;

fiber optic IO surface plasmon resonance as described by A. Abdelghani et al. (1997) in *Sensors and Actuators B* 38, pages 407–410;

surface plasmon resonance as described by H. Kano and S. Kawata (1994) in *Applied Optics* 33, pages 5166–5170;

leaky mode spectroscopy as described by Osterfeld and H. Franke (1993) in *Appl.Phys.Lett.* 62, pages 2310–2312;

resonant mirror as described by R. Cush et al. (1993) in *Biosensors Bioelectronics* 8, pages 347–353.

Nematic liquid crystals suitable for the present invention are known in the art, and are disclosed e.g., in DE 24 29 903 (U.S. Pat. No. 4,041,847) or in DE 37 32 284 (U.S. Pat. No. 5,324,449) and in numerous other documents. Examples are phenylpyrimidine derivatives or fluorosubstituted phenylcyclohexane derivatives as they are disclosed in the examples of those patents. Liquid crystals can be used as single substances or as mixtures and can optionally be used in gel form. The liquid crystal materials have to be selected with regard to their refractive indices: At least one of the refractive indices of their nematic phase and the refractive index of their isotropic phase has to be lower than the refractive index of the waveguide of the measuring device, in order to allow the use of evanescence field effects. Furthermore the liquid crystals have to be selected with regard to their clearing point. Preferred liquid crystals are selected so that their clearing point is slightly higher than room (respective ambient) temperature, because the order parameter changes strongly near the clearing point. This non-linear behavior of the order parameter can be used to enhance the sensitivity of the detection device.

In order to prepare an oriented liquid crystal layer the substrate is first covered with an orientation layer, e.g. a rubbed polyimide layer, as described above. Other orientation layers and methods of their application are known in the art, e.g., by F. J. Kahn in *Appl. Phys.Lett.* 22, 386–388 (1973). Methods to apply the liquid crystal layer are also known in the art, and are described e.g., by S. J. Petrash and E. T. Zellers in *Analyt.Chim.Acta* 288 167–177 (1994) and by J. Cognard: "Alignment of nematic liquid crystals and their mixtures" *Mol. Cryst. Liq.Cryst.* 78, Suppl 1.1 (1982).

The thickness of the liquid crystal layer is preferably 0.5–100 um, more preferably 1–10 um, particularly preferably 2–6 um. The thickness of the orientation layer is preferably 10–500 nm, particularly preferably 50–150 nm.

Figure 1:
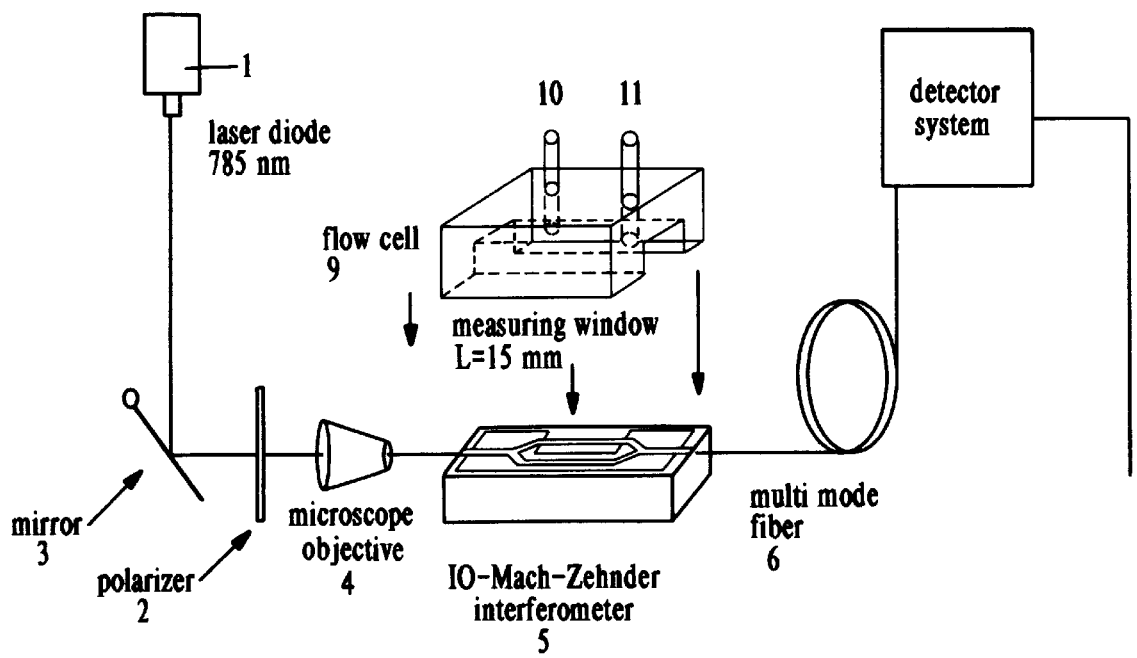
FIG. 1 depicts the experimental set-up for measuring the interaction between analytes and LC phase using a Mach-Zehnder interferometer.

The inventors have shown that the birefiingence of LC-layers, which is related to the order parameter of said LC-layers, can be disturbed by an analyte and that this disturbance can be measured using a Mach-Zehnder interferometer. FIG. 1 depicts the experimental set-up: The light path contains laser diode (1) emitting at 785 nm wavelength, a polarizer (2) and a mirror (3), a microscope lens (4) for coupling the light to the miniaturized Mach-Zehnder interferometer (5) and a detector system (7) connected to the miniaturized Mach-Zehnder interferometer (5) by multi mode fiber optics (6). The data were collected and analyzed by a micro computer (not shown). The Mach-Zehnder interferometer is embedded in a flow cell (9). This flow cell has an inlet (10) and an outlet (11) for the gas to be monitored. The Mach-Zehnder interferometer used is shown in more detail in FIG. 2; it was prepared as an integrated optical device based on strip waveguides. The light from a laser diode is in-coupled into a waveguide (12) and travels to the first y-branch coupler (13), dividing the light beam into a measuring arm (14) and a reference arm (15). The two beams are joined in a second y-branch coupler (16) and leave the interferometer device through waveguide (17). The whole interferometer is produced on a BGG36 glass slide. The strip waveguides were produced by an ion exchange process. The interferometer chip is covered with a patterned $SiO_2$ layer (not shown) with an opened window in the measuring arm. A nematic liquid crystal film was deposited on the interferometer by a spin coating process. This film was parallel aligned by an unidirectional rubbed polyimide layer. The interferometer described above was designed and produced by IOT (Waghaeusel, Germany) based on literature: L. Ross, "Integrated Optical Components in Glass Substrates" *Glastechn. Berichte* 62, pp. 285 f (1989), and U. Hollenbach, C. Estathiou, N. Fabricius, H. Oeste, and H. Goetz, "Integrated Oprical refractive Index Sensor by Ion-exchange in Glass" *Proc. SPIE-Int. Soc. Opt. Eng.* (*Micro-Opt.*) 1014, pp 77 f (1988).

Figure 3:
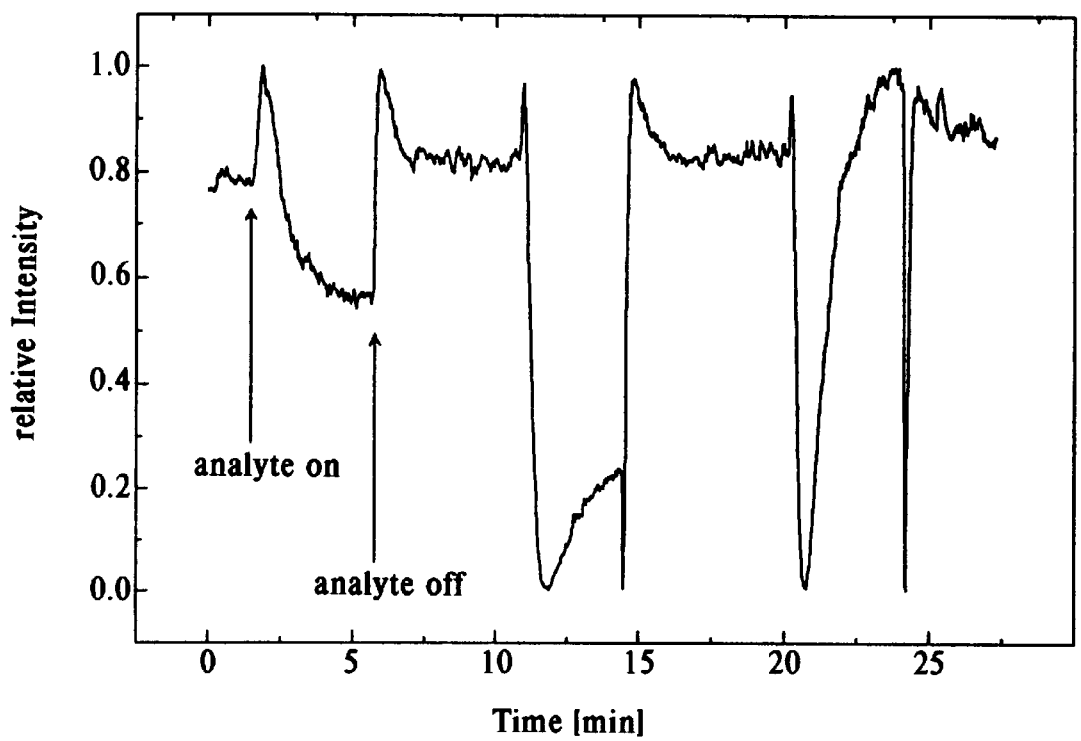
FIG. 3 shows interferometer responses of synthetic air, and with 1200 ppm, 1600 ppm, and 1800 ppm p-xylene in synthetic air.

Interferometer responses of synthetic air, and with 1200 ppm, 1600 ppm, and 1800 ppm p-xylene in synthetic air using the Mach-Zehnder interferometer described above are depicted in FIG. 3. Calibration graphs (phase shift vs. concentration) for p-xylene using two different LC films containing the LC components shown in the formulae are given in FIG. 4. Calibration graphs for m-xylene and for p-xylene are given in FIG. 5. The calibration graph of p-toluene shows a phase transition at about 6,000 ppm (see FIG. 6): Below that phase transition the curved portion of the calibration graph ends with a discontinuity and at concentrations higher than the phase transition the calibration graph is linear.

In preferred embodiments of the invention, alternative devices and methods useful to monitor contaminants in very low concentration ranges are provided. Examples of such embodiments are described as follows.

It was shown that grating couplers can be used to monitor the changes in refractive index. Details of the underlying principle are given above; further details can be found in Example 3.

In some cases the detection limits which could be achieved with the procedures described above proved to be insufficient. For example, the maximum level of p-xylene allowed in the air at working places is 100 ppm, whereas the limit of detection in an embodiment above was 500 ppm. It was surprisingly found that a major improvement in sensitivity was possible when the LC phase was first doped with an isotropic material. Thus, the working point of the system is moved closer to the region of the phase transition and the so modified LC phase reacts with a detection limit much lower than without modification. Basically any isotropic material soluble in the LC mixture and different from the compound to be detected can be used. Examples for isotropic materials useful for doping the LC phase in order to adjust the detection limit are tetrachloroethylene (TCE), cyclohexane, o- or p-xylene, toluene, acetone, tetrahydrofuran, alcohols, like ethanol or higher alcohols, biphenyl, phenylcyclohexane, isopropylbenzene. Preferred as isotropic materials are solvents like TCE. The amount of dopant used is preferably 0–80 wt. %, more preferably 0–40 wt. %, particularly preferably 1–20 wt. %.

Furthermore by adjusting the concentration of the isotropic material the sensitivity of the system can be adapted to the specific analytical problem; for the detection of p-xylene the point of phase transition can be modified as follows:

| dopant: ppm TCE | 0 | 3610 | 4300 |
|---|---|---|---|
| phase transition at . . . ppm p-xylene | 2140 | 643 | 100 |

Examples of response curves are given in FIGS. 9 and 10.

In order to monitor threshold values for a contaminant a highly simplified device was developed. This device allows, e.g., visual interpretation and is described in detail in Example 4.

Without further elaboration, it is believed that one skilled in the art can, using the preceding description, utilize the present invention to its fullest extent. The preferred specific embodiments and examples are, therefore, to be construed as merely illustrative, and not limitative of the disclosure in any way whatsoever.

The entire disclosures of all applications, patents, and publications cited above and below, are hereby incorporated by reference.

EXAMPLES

In the foregoing and in the following examples, all temperatures are set forth uncorrected in degrees Celsius; and, unless otherwise indicated, all parts and percentages are by weight.

Example 1

Liquid crystal materials and coating

Nematic liquid crystal materials used were materials as disclosed in DE 24 29 093 and in DE 37 32 284 (U.S. Pat. No. 5,324,449) especially liquid crystals or mixtures containing phenylpyrimidine derivatives like PYP-606 and PYP-701, or fluorosubstituted phenyl-cyclohexane derivatives like IS 4655; these materials were from Merck KGaA, Darmstadt, Germany.

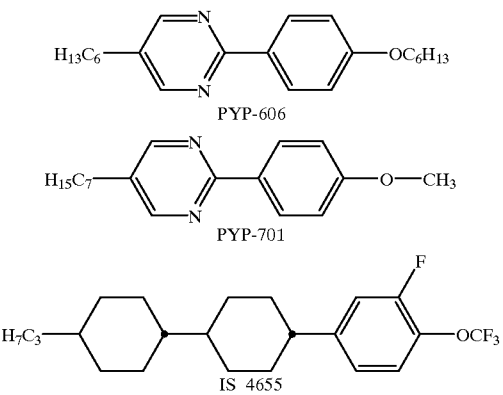

In order to achieve a uniform homogeneous planar orientation of the liquid crystals the sensor devices were first covered with an unidirectional rubbed polyimide layer: A 3% solution of the polyimide AM4075 (Merck KGaA, Darmstadt, Germany) in cyclopentanone was spin-coated at 4000 U min$^{-1}$ for 20 sec. and heated for 2 hours at 100° C. under vacuum. After the rubbing procedure the liquid crystal films were deposited upon the sensor devices by spin-coating at 2000 U min$^{-1}$ for 20 sec.

Example 2
Mach-Zehnder interferometer

The integrated optical Mach-Zehnder interferometer used was designed and produced by IOT (Waghaeusel, Germany) based on literature: L. Ross, "Integrated Optical Components in Glass Substrates" *Glastechn. Berichte* 62, pp. 285 f. (1989), and U. Hollenbach, C. Estathiou, N. Fabricius, H. Oeste, and H. Goetz, "Integrated Oprical refractive Index Sensor by Ion-exchange in Glass" *Proc. SPIE-Int. Soc. Opt. Eng. (Micro-Opt.)* 1014, pp 77 f. (1988).

The waveguides were made by an Ag$^+$ ion exchange process on BGG 36 glass. After ion-exchanging in a 10% (w:w) Ag salt melt the devices were additionally tempered at 250 EC for 90 minutes. A strip waveguide single moded at the operation wavelength of 785 nm and a peak change in refractive index of $\Delta n=0.075$ was obtained by this treatment. The surface of the interferometer was covered with a patterned SiO$_2$ layer using a plasma impulse CVD process. Thus, only within the silica free window of 15 mm in length on one of the interferometer arms the evanescent field of the guided light can be influenced by the sensing LC-layer. The experimental set-up is outlined in FIG. 1. A laser diode operating at 785 nm (HC 7812G, Hitachi, JP) was used as light source. The TE-mode was irradiated by linearly s-polarized light which was end-fire coupled into the interferometer chip using a microscope objective (ZEISS 10×40; ZEISSS, Oberkochen, Germany). The output light was butt end coupled into a multi mode fiber and detected with a diode spectrometer (ZEISS MCS 240; Oberkochen, Germany). The Mach-Zehnder chip and all components used for the light in-coupling and out-coupling were mounted on separate micro positioners (Photon Control). Data acquisition was carried out with a PC using a 12-bit A/D card.

Figure 2:
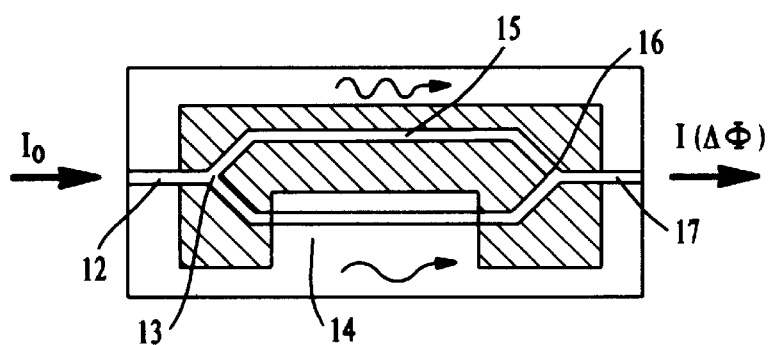
FIG. 2 shows the Mach-Zehnder interferometer in more detail.

Details of the Mach-Zehnder interferometer chip are given in FIG. 2.

Example 3
Grating Coupler

The grating coupler chips (ASI-3200; Artificial Sensing Instruments, Zurich, Switzerland) were equipped with a single mode waveguide (21) made of Ta$_2$O$_3$ with n$_D$=2.22 and 157 nm in thickness on a glass substrate (22). The grating (23) is 1 mm in length with a grating period of 0.75 $\mu$m. The chips were used as a reflection grating coupler. The linearly polarized light from a He—Ne laser (24) ($\lambda$=633 nm) was focused upon the grating in order to irradiate the TE waveguide mode, using a lens (25) and mirrors (26), (27). When the coupling condition of equation 2 (above) is met a part of the light travels through the waveguide and causes a minimum in the reflected intensity distribution. The intensity of the reflected light is observed with a one dimensional CCD array (28). A change in the refractive index of the sensitive material upon the grating changes the coupling conditions and leads to a change of the minimum position on the CCD array. The CCD signal was converted into a 12 bit signal and read out with a personal computer. The minimum in the reflected intensity distribution is determined by means of the so-called center of gravity method.

The reflection grating coupler is equipped with a flow cell (29) with an inlet (30) and an outlet (31) for the gas to be analyzed.

The grating coupler is depicted in FIG. 7.

Calibration curves prepared for different analytes using the above grating coupler are depicted in FIG. 8.

Example 4
Threshold Monitoring Device

A simple device especially for visually monitoring threshold values of contaminants in gases is depicted as a sectional view in FIG. 11. The device is based on a gas cuvette with an inlet (41) and an outlet (42) for the analyte. It is equipped with two windows (43) and (44); on the interior side of the gas cuvette one of these windows (44) is covered with an orientation layer (45) and with a layer of liquid crystals (46). Outside the gas cuvette there are two polarizer foils (47 and 48) orientated in crossed formation. Consequently, if the LC layer (46) is in its isotropic state no light will be transmitted; light is only transmitted if the LC layer (46) is in its ordered bi-refringent state. By selecting the LC-material, and a suitable dopant if necessary, the clearing point can be adjusted, so that the phase transition occurs at a predefined concentration of analyte.

The device is presented as a variant for direct view. However, using a mirror it can simply be modified to be used in a reflective mode.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An optical transducer for measuring and/or detecting a contaminant in a gas, which comprises:
   a liquid crystalline phase as a sensing element in contact with a flow cell for said gas, the liquid crystalline phase being a nematic crystalline phase on an orientation layer; and
   means for measuring and/or detecting changes of the refractive index of said liquid crystalline phase caused by interaction of said contaminant with said liquid crystalline phase.

2. The optical transducer of claim 1, wherein said crystalline phase is doped with an isotropic material.

3. The optical transducer of claim 1, wherein said means for measuring and/or detecting changes of the refractive index is a Mach-Zehnder interferometer.

4. The optical transducer of claim 1, wherein said means for measuring and/or detecting changes of the refractive index is a grating coupler.

5. The optical transducer of claim 1, wherein said means for measuring and/or detecting changes of the refractive index is provided by placing said flow cell between two linearly polarizing means, whereby the two axes of polarization are crossed.

6. A method for measuring and/or detecting the concentration of a contaminant in a gas which comprises:
   providing the gas in a flow cell having on at least part of an inner wall of the cell a nematic liquid crystal layer, as a sensing element, on an orientation layer for the liquid crystal layer;
   measuring and/or detecting changes of the refractive index of said nematic liquid crystal layer caused by the presence of the contaminant in the gas in the flow cell.

7. The method of claim 6, wherein said nematic liquid crystal layer is doped with an isotropic material.

8. The method of claim 6, wherein changes of the refractive index are measured and/or detected using a Mach-Zehnder interferometer.

9. The method of claim 6, wherein the changes of the refractive index are measured and/or detected using a grating coupler.

10. The method of claim 6, wherein the changes of the refractive index are visually detected by placing said flow cell between two linearly polarizing means, whereby the two axis of polarization are crossed, such that a change in the refractive index to a certain threshold is visually detectable.

11. The method of claim 6, wherein the gas is contaminated air.

12. The method of claim 6, wherein the contaminant is an aromatic or aliphatic solvent or a halocarbon.

13. The optical transducer of claim 1, wherein the liquid crystalline phase contains a phenylpyrimidine or fluoro-substituted phenyl-cyclohexane liquid crystal compound.

14. The method of claim 6, wherein the liquid crystal layer contains a phenylpyrimidine or fluoro-substituted phenyl-cyclohexane liquid crystal compound.

15. The optical transducer of claim 1, wherein said means for measuring and/or detecting changes of the refractive index is a device for visual or photometric detection.

16. The method of claim 6, wherein changes of the refractive index are measured and/or detected by a device for visual or photometric detection.

17. The optical transducer of claim 1, wherein the nematic liquid crystalline phase has a clearing point slightly higher than ambient temperature.

18. The method of claim 6, wherein the nematic liquid crystal layer has a clearing point slightly higher than ambient temperature.

19. The optical transducer of claim 1, wherein the nematic liquid crystalline phase has a layer thickness of 0.5 to 100 $\mu$m.

20. The method of claim 6, wherein the nematic liquid crystal layer has a thickness of 0.5 to 100 $\mu$m.

21. The optical transducer of claim 1, wherein the orientation layer has a thickness of 10 to 500 nm.

22. The method of claim 6, wherein the orientation layer has a thickness of 10 to 500 nm.

23. The optical transducer of claim 2, wherein the isotropic material is tetrachloroethylene, cyclohexane, o- or p-xylene, toluene, acetone, tetrahydrofuran, an alcohol, biphenyl, phenylcyclohexane or isopropyl benzene.

24. The method of claim 7, wherein the isotropic material is tetrachloroethylene, cyclohexane, o- or p-xylene, toluene, acetone, tetrahydrofuran, an alcohol, biphenyl, phenylcyclohexane or isopropyl benzene.

25. The optical transducer of claim 2, wherein the isotropic material is provided in an amount of 1-20% by weight.

26. The method of claim 7, wherein the isotropic material is provided in an amount of 1–20% by weight.

* * * * *